United States Patent
Hwang et al.

(10) Patent No.: US 8,956,842 B2
(45) Date of Patent: Feb. 17, 2015

(54) PAENIBACILLUS SP. HPL-3 STRAIN PRODUCING XYLANASE HAVING HEAT-RESISTANCE, A WIDE RANGE OF OPTIMUM PH AND HIGH ACTIVITY, A NOVEL XYLANASE SEPARATED FROM THE STRAIN, AND A METHOD FOR MASS-PRODUCTION OF THE SAME USING THE TRANSFORMANT ORIGINATED FROM THE STRAIN

(75) Inventors: In Taek Hwang, Daejeon (KR); No Joong Park, Daejeon (KR); He Kyoung Lim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/111,647

(22) PCT Filed: Aug. 12, 2011

(86) PCT No.: PCT/KR2011/005966
§ 371 (c)(1),
(2), (4) Date: Oct. 14, 2013

(87) PCT Pub. No.: WO2013/024909
PCT Pub. Date: Feb. 21, 2013

(65) Prior Publication Data
US 2014/0038262 A1    Feb. 6, 2014

(51) Int. Cl.
*C12N 9/12*       (2006.01)
*C12N 15/00*    (2006.01)
*C12N 1/20*       (2006.01)
*C07K 1/00*       (2006.01)
*C12N 9/24*       (2006.01)
*A23K 1/165*     (2006.01)
*A23K 1/18*       (2006.01)

(52) U.S. Cl.
CPC ............ *C12N 9/2482* (2013.01); *A23K 1/1653* (2013.01); *A23K 1/1813* (2013.01); *C12N 9/248* (2013.01); *A23K 1/1826* (2013.01); *C12Y 302/01008* (2013.01)
USPC .... 435/195; 536/23.2; 435/320.1; 435/252.3; 530/350

(58) Field of Classification Search
USPC .................... 435/195, 320.1, 252.3; 530/350; 536/23.1
See application file for complete search history.

(56) References Cited

U.S. PATENT DOCUMENTS

2008/0248160 A1    10/2008    Steer et al.

FOREIGN PATENT DOCUMENTS

| WO | 96/02632 A1 | 2/1996 |
| WO | 97/14803 A1 | 4/1997 |
| WO | 97/22692 A1 | 6/1997 |

OTHER PUBLICATIONS

GenBank Accession No. ADX97440: Xylanase KRICT PX3 [*Paenibacillus terrae* HPL-003]2011.02.23; 2 pages.
International Search Report; mailed Apr. 20, 2012; PCT/KR2011/005966.

*Primary Examiner* — Maryam Monshipouri
(74) *Attorney, Agent, or Firm* — Ladas & Parry LLP

(57) ABSTRACT

The present invention relates to the novel *Paenibacillus* sp. strain, and the novel protein isolated from the same. More particularly, the present invention relates to the novel *Paenibacillus* sp. strain producing xylanase, and the novel xylanase having high activity at high temperature and in a wide range of pH, and a production method of the same. The *Paenibacillus* sp. HPL-3 strain (KCTC11987BP) and the xylanase of the present invention demonstrates high activity at high temperature or in a wide range of pH to decompose xylan, the major component of various lignocellulosic biomass, so that they can be effectively used for the production or development of bio-fuel, alternative material, performance chemical, bio-polymer, food and feeds, etc.

6 Claims, 7 Drawing Sheets

SDS-PAGE analysis.
M : Marker,
lane 1 : PX3 cell lysate,
lane 2 : Only PX3

SEQUENCE LISTING

```
<160> NUMBER OF SEQ ID NOS: 6

<210> SEQ ID NO 1
<211> LENGTH: 1393
<212> TYPE: DNA
<213> ORGANISM: Paenibacillus sp.

<400> SEQUENCE: 1
ggctcaggac gaacgctggc ggcgtgccta atacatgcaa gtcgagcggg gttatgttaa      60
aagcttgctt ttaacataac ctagcggcgg acgggtgagt aacacgtagg caacctgccc     120
atcagactgg gataactacc ggaaacggta gctaataccg gatacatcct ttccctgcat     180
ggggagagga ggaaagacgg agcaatctgt cactgatgga tgggcctgcg gcgcattagc     240
tagttggtgg ggtgaaggcc taccaaggcg acgatgcgta gccgacctga gagggtgatc     300
ggccacactg ggactgagac acggcccaga ctcctacggg aggcagcagt agggaatctt     360
ccgcaatggg cgaaagcctg acggagcaac gccgcgtgag tgatgaaggt tttcggatcg     420
taaagctctg ttgccaggga agaacgtctt gtagagtaac tgctacaaga gtgacggtac     480
ctgagaagaa agccccggct aactacgtgc cagcagccgc ggtaatacgt aggggggcaag     540 cgttgtccgg aattattggg cgtaaagcgc gcgcaggcgg ctctttaagt ctggtgttta     600
atcccgaggc tcaacttcgg gtcgcactgg aaactgggga gcttgagtgc agaagaggag     660
agtggaattc cacgtgtagc ggtgaaatgc gtagatatgt ggaggaacac cagtggcgaa     720
ggcgactctc tgggctgtaa ctgacgctga ggcgcgaaag cgtggggagc aaacaggatt     780
agataccctg gtagtccacg ccgtaaacga tgaatgctag gtgttagggg tttcgatacc     840
cttggtgccg aagttaacac attaagcatt ccgcctgggg agtacggtcg caagactgaa     900
actcaaagga attgacgggg acccgcacaa gcagtggagt atgtggttta attcgaagca     960
acgcgaagaa ccttaccagg tcttgacatc cctctgatcg gtctagagat agatctttcc    1020
ttcgggacag aggagacagg tggtgcatgg ttgtcgtcag ctcgtgtcgt gagatgttgg    1080
gttaagtccc gcaacgagcg caaccctta gcttagttgc cagcaggtca agctgggcac    1140
tctaagcaga ctgccggtga caaaccggag gaaggtgggg atgacgtcaa atcatcatgc    1200
cccttatgac ctgggctaca cacgtactac aatggccggt acaacgggaa gcgaaagagc    1260
gatctggagc gaatcctaga aaagccggtc tcagttcgga ttgcaggctg caactcgcct    1320
```

| | |
|---|---:|
| gcatgaagtc ggaattgcta gtaatcgcgg atcagcatgc ccgcggtgaa tacgttcccg | 1380 |
| ggtcttgtac aca | 1393 |

```
<210> SEQ ID NO 2
<211> LENGTH: 6956
<212> TYPE: DNA
<213> ORGANISM: Paenibacillus sp.

<400> SEQUENCE: 2
```

| | |
|---|---:|
| catcctctct ataagcttaa cagaagccta gcccaataga caaagacgg gtataccgtc | 60 |
| cccggtcccg tcttttctta tcatgaatcg ctgctgtata tgccaggcga gctggaagtg | 120 |
| aattgcgctt caaccttatt tcttggttgt tgttactact ttagctgctg cttttggagc | 180 |
| tgttttcact gctgtttttg gagctgtttt taccactgtt tttgctggag tcactttttt | 240 |
| aacaggagct ttgtgagccg ctttttagc tacaacatgg tgtgcacgag ttttgtgagc | 300 |
| tgttgcttta tgttttactg cataatgtct tttagcatga tgtttaacgg tacggtgctt | 360 |
| cgcttttaca gcttttgctt tatgtgccgt ttttttggca acagcttttt tggcaggagc | 420 |
| ttttttagct gttgttactt tatgagctgt tgcagctttt ttaacaggtg ctttcaccac | 480 |
| tggtgttttc gtcgcaggtg cttttactgc tggtgctttg gtagccgggg tcgtaaccgc | 540 |
| cggtgctttc gttgctggtg cagttgtagc tggcgttgtt gtcgctgtag cggcgaatgc | 600 |
| actgcttgct cctcccaata cgcttactac ggtcaatacg gctgctgcat ttttagtcca | 660 |
| ttttttcatg attgtatcac ctctcctta aagtatcttt agcttatcag gagaattcgg | 720 |
| gataattgtg gaacaaatgt gtgaaaagta tatgaaaaag cgtgcagccc cgtattcaaa | 780 |
| aaatacgtga gtctgcacgc tgtacgtttt acacaattac attcactaac cgatggcaat | 840 |
| ccaggaaaca ataccgtagt tgtgcgcggt ttcgttccat ttggttacta caatcaccgc | 900 |
| tccattcggc gtctgcgatt tcagcgtcgc atgaaagaga ggatggttcg tcatcgctac | 960 |
| cagcgtatag tccgggttca taaaaggctc tgcaatata atgatcactt ccgtctctcc | 1020 |
| ttcgctgccc ttcaaaagaa acggcgctct gccaaactgc tgcaatgcgg actgattggc | 1080 |
| acaagtacga accggggtga tgctcagatg ctccggcttc actgcgttca gctccagctc | 1140 |
| acgcgagcct acggagcctt ccaccagatg atgcccttca atgctttgct ctgccaagtg | 1200 |
| atggcttttgt accgcagcgg tctgtagatg ctccgatcct acagcttccg ggctcagcac | 1260 |
| ctcgctgtcg acggcctgag cttttcagatg gctgcgagat acactatctg cctggagtct | 1320 |
| gtcgccactg ataccttcct ccggcaaaag ccccgagaga tgaatgtccg tggacaactg | 1380 |
| agccagcgtc actgcgcccg gcttcaggtg gtgcgcatca atggcttctg ctccaatgtg | 1440 |
| tcggccttca atggcttcct cagccacatg ctgggactgt accgctccat ttgcaagctt | 1500 |
| gccggacgta accgcttctt cttgcaatgt gtcttccgac accacctgcc agcctatatg | 1560 |
| ctgcggctgg atggcacctg cttgcagatg ctccgactgg acggaatcca aggcgatatg | 1620 |
| ccttgattgc accgcgcctt ctgccagcgc cgattcctgt accgcccat cggccagatg | 1680 |
| aaggtggtgt accgcttgct ccaccagatg tacggagctt acgctggctt ccgccaaatt | 1740 |
| cgaagcacgc accgcccgaa gcgcaagctt ctcagcattc acgctcccgg cctggagcgc | 1800 |
| gtgaacagat acacttcccg gcgcaatatg ccgggtcatc actgctgaag cctgcaaatg | 1860 |
| gtcagaggtg acggcttccg ggccaaatg gctcgattgg atcgcctctt ctgccaaatg | 1920 |
| gttcccttgc accgcttcgt ccgtaatgtg ccatggctgt accgagtggg cggacagctt | 1980 |
| ggccggccgt cacgctctca tccgccagtt tgccggacgt aacagactca tcctgcaagg | 2040 |

```
catcggtcga tatcgcctgt gatgcgatat gctcgctctg aatggttccg atgtgcagat    2100
gatgtggctg gatggactcc ggtgcgtat gcacggactt cactgccccc tctgccagcg    2160
ctctgtcctg taccgctcca tctgccagat gccggggtg tacggcctgc gcagacaaat    2220
gtgaagggcc gacgatgcct tccgcgaggt tggtcgcttg cacggcccga gccgccagct    2280
tctccgaggt gacgctttcc gcttgaagcg cacgaccgga tacgctatcc ggggccagat    2340
gtctcgtaag caccgccgaa gcctgcaaat ggtcagaggt gacggcttcc ggggccaaat    2400
ggctcgattg gatcgcttct tctgccaaat ggttcccttg caccgcttcg tccgtaatgt    2460
gccatggctg taccgagtga gcggacaact tggcggccgt cacactctca tccgccagtt    2520
tgtcagacgt aacagactca tcctgcaagg catcggtcga tatcgcctgt gatgcgatat    2580
gctcgccctg aatggttccg atgtgcagat gatgtggctg gatggactcc ggtgcgtat    2640
gcacggactt tactgcccct tctgccagcg ctctgtcttg taccgctcca gctgccaaat    2700
gccggggtg tacggcctgc gcagacaaat gtgaagggcc gacgctgcct tccgcgagat    2760
tcgtcgcttg caccgagcgt gctgccagct tttccgaggt gatgctttcc gcttgaagcg    2820
cacgatcgga tacactatcc ggggccagat gtctcgtatg caccgacgaa gactgtaaat    2880
gaaccgaggt gaccgcttcg gctgccagat gtgtcgaatc cacagccgcc acagccaggt    2940
gactgctttg tacagcttca tctgtaatat gctcggactg cactgcatgg gcagatagct    3000
tgatggaggt tacacttcct ccgccagttt gtcggacgta acagactcat tctgcaaagc    3060
atcggtcgat atcgcctgtg atgtgatatg ctcgccctga atggttccga tgtgcagatg    3120
gtgcggctgg atagactccg gtgcgatgtg cacggacttc actgccccct ctgccagcgc    3180
tctttcctgt accgctccaa ctgctagatg ccgggggtgt acggcctgcg cagataaatg    3240
cggaggaccc acgctgcctt ccgcgaggtt cattccttgt accgagcgcg ccgccagctt    3300
ttccgaggta atgctttctg cttgaagcgc acgaccggat acgctatccg gggccagatg    3360
tctcgtaagc accgtggagg cttgtagatg taccgaggtg accgctccgg ccgccagatg    3420
cgccgaatcg acagccgcca cagccagatg gttgcttctc ctgattcgtg agctggggat    3480
gcttggaagc ttctgggtgt atatcgtgcc tgggctgatc ggggtgttca atgtgattgt    3540
aattcgctcc tttattgagg gcttaccgga agggatcttg gagtcggcgc gtatagatgg    3600
ggcggggag tttgcgactt ttatgcgtat cgttttgccg ctatgtgtcc cggtgctggc    3660
aacggtgtcg ctgttcacgg cagtagcgca atggaactcc tggttcgatg tattttttgta    3720
caattcgtcg tatgagcagt ggagtaccct ccagtatgag ctgatgaaaa tattgcaaaa    3780
ttccaacacg tccgtgaacg ctcaggatta tgccagccaa ttcgcaggct cggaaaatct    3840
ggcgaaggcg gttactccta cctccattcg tgccacgatg acaattgtgg cgtctgtgcc    3900
tattattttg gtctatccat ttttgcagaa atattttgtg aagggtatga ctttgggcgg    3960
tgtcaaggga taagcaagga ccggaaatgt gtgaaactcg ctttcttata ttttgaaaat    4020
atgggcgtag gagggattgc gttgaggtca ttttgtata aatctttggg tctggtgctg    4080
gtcggggtgt tgttattgcc agtggggtgg tggggctgt ctgtagcgga ggcgactcca    4140
actgtgaaac attcccagtc agttgcggat acggttctgt cgacggggag cgtgaataag    4200
accatcggga cgtatggatt tgagcaaggc aacgttgagg gctggaagcc tcggggact    4260
tatcccaaa tcgcaaccgt ctcagaagct gcatatggcg gcgtacacag cctgaaggta    4320
accgctcgca cggaggtttg gaacggtgcg gagctggatg tgaagtcgct gttgcagccg    4380
```

```
ggtgtggaat atgagattag cggctatgtg aagcaggacg gtaattctac gacgccgagc    4440
gtgattaagt ttacggtgga gcagcagccg acaggcgggg ccacgacatg gaagacggtt    4500
gcgcagacag agacgacgga tacatcgtgg gccaaacttc aagggacata tacattcacc    4560 gggggatgg atacattgaa gttgtatgtg gaaagctcga atcctgcaca ggcctattat    4620
ctggatgagg tggaaatcag gcaggtgtcg gagacaccaa ccactccccc aacggagccg    4680
acaagtggta tcgaatccag atttgaagat ggtacggctc aaggctgggt atcccgtatg    4740
ggcaccgaga cggtgcaggt gtcgaatgcc gatgcacgaa ccggatcgta cagtctgttg    4800
acgacaggca gacaacaaac atatgccggg ccaaagctgg acgtgactgc tacagtgcaa    4860
aaaggcagcc gttacacggt cagcgcttgg gtaaagctgg caccgggcga gcagcagcct    4920
gccaaggtgc gcctcagcgt acagcgcgat catcaaggtg aaagtacgta tgaaactgtg    4980
gtaggcaaca cggccatcac gactgggga tggacgcatt tgtacggaac gtatactctc    5040
gcgcatgagg cagacaccgt ctctatgtat ttggaaacgc cagaaggtac ggcttccttt    5100
tacatggatg atttcgagct gtcgcttgtg ccgccgttgg ctattgagaa ggacattccc    5160
tctttgcatg gattgtatca gggacagttc agcatcggta cggctattga agctttccag    5220
acagaagggg cttacgggga gctggtgcag aagcattta acagcgtcgt cgccggaaat    5280
gcgatgaagc cgatctcctt gcagccgtcc gaaggacagt tccattggga agaagcagac    5340
cggattgtgc aatttgccca gcagcatggg attgctatcc gtttccatac actggtgtgg    5400
cataaccaga ccggcgattg gatgtttaag gataagaatg gacagccgat gacgccgacc    5460
gcggaaaata aaaagctttt gctggatcgg ctggagacgc atattcgtgc tgttgcagcc    5520
cgttataaaa atgtaatcac cgattgggat gtggtgaatg aagtcattga tcccgaccag    5580
ccggacggta tgcgccgcag caagtggtat cagattaccg gcacggatta tattgacaaa    5640
gcattccgtg tcacgaggga agcggcgggt ccgaacgccc ggctgtacat taacgattac    5700
aacacgcatg aaccgaagaa acgggatttt ctgtacaatt tggtgcgtga tttactcgct    5760
aaaggcgtac cgatcgatgg cgtaggtcac caatcgcata tccgcctgga gttccctgct    5820
attgacgaga tggagcagtc tattgaaaag tttgcttcgc tcggcctgga taatcagatc    5880
acggagctgg atatgggcct gtattctaat gatacagacc actacgaaac gatacctgaa    5940
gccatgctga tccggcaggc tcaccgctat cgggcgttgt tcgatatgtt ttcccgacag    6000
caggagcata tcagtaatgt gacgatttgg ggtacggatg atggaaatac gtggctcagt    6060
atgttcccga ttgcccggct ggataagccg ctgctgttcg acgaacggtt aaaggccaaa    6120
tatgcctatt gggcgcttgt tgacccgtcc aaagtaccgc cgctgccagc ggggagcaac    6180
gaatagcaac ataggtatgg attacacgtg gaaatcattt ctatacacca aaaaggcagg    6240
ccgcctctga catgccacaa ggacatgcga aggacgatct gccttttact gtaaaataat    6300
acgatctcta ctccagattg gcgtgttgac caaacataga ttcagaagtc agcttgcgta    6360
gctccatcgt tctgagcacc aatgcatcgc catacagcag caaggtttgc tcaaatagtg    6420
aacccatggg ctgaatggtt tggtaatcct tgttggatgg atccttgggt gcgcccggaa    6480
gcctgacgat aatatcagcc agcttgccaa tggtcgatcc aggggaggtg gtcagaagtg    6540
ccagagaagc ccccagcttt ttcgtctttt ctgccatcga ggtcaaactt tggtttcac    6600 cagagcctga accgataatc agcaagtcac cttcgcccaa acctggagtt actgtttccc    6660
cgaccacata agcctgaaca cccatatgca tcagccgcat cgccagcgaa cggatcatga    6720
atccagaacg gcctgcgcct gcgacgaaca ccttattcgc tgaggtaatg gactggatca    6780
```

```
gttgctctga ttcctcatca ttgattagct gtggaaccaa ttgcagttcc ttgagcacct    6840
cggataaata ttgagaggtt tccattggaa ttaaccttgt ttaatgagct gctgcatttc    6900
ggaagcaacg gccttttgt cgtcctcacc agtgatcccg ccgccaacaa taacca         6956
```

<210> SEQ ID NO 3
<211> LENGTH: 1620
<212> TYPE: DNA
<213> ORGANISM: Artificial Sequence
<220> FEATURE:
<223> OTHER INFORMATION: SLX-09

<400> SEQUENCE: 3

```
atggatacat tgaagttgta tgtggaaagc tcgaatcctg cacaggccta ttatctggat     60
gaggtggaaa tcaggcaggt gtcggagaca ccaaccactc ccccaacgga gccgacaagt    120
ggtatcgaat ccagatttga agatggtacg gctcaaggct gggtatcccg tatgggcacc    180
gagacggtgc aggtgtcgaa tgccgatgca cgaaccggat cgtacagtct gttgacgaca    240
ggcagacaac aaacatatgc cgggccaaag ctggacgtga ctgctacagt gcaaaaaggc    300
agccgttaca cggtcagcgc ttgggtaaag ctggcaccgg cgagcagca gcctgccaag    360 gtgcgcctca gcgtacagcg cgatcatcaa ggtgaaagta cgtatgaaac tgtggtaggc    420
aacacggcca tcacgactgg gggatggacg catttgtacg gaacgtatac tctcgcgcat    480
gaggcagaca ccgtctctat gtatttggaa acgccagaag gtacggcttc cttttacatg    540
gatgatttcg agctgtcgct tgtgccgccg ttggctattg agaaggacat tccctctttg    600
catggattgt atcagggaca gttcagcatc ggtacggcta ttgaagcttt ccagacagaa    660
ggggcttacg gggagctggt gcagaagcat tttaacagcg tcgtcgccgg aaatgcgatg    720
aagccgatct ccttgcagcc gtccgaagga cagttccatt gggaagaagc agaccggatt    780
gtgcaatttg cccagcagca tgggattgct atccgtttcc atacactggt gtggcataac    840
cagaccggcg attggatgtt taaggataag aatggacagc cgatgacgcc gaccgcggaa    900
aataaaaagc ttttgctgga tcggctggag acgcatattc gtgctgttgc agcccgttat    960
aaaaatgtaa tcaccgattg ggatgtggtg aatgaagtca ttgatcccga ccagccggac   1020
ggtatgcgcc gcagcaagtg gtatcagatt accggcacgg attatattga caaagcattc   1080
cgtgtcacga gggaagcggc gggtccgaac gcccggctgt acattaacga ttacaacacg   1140
catgaaccga gaaacggga ttttctgtac aatttggtgc gtgatttact cgctaaaggc    1200
gtaccgatcg atggcgtagg tcaccaatcg catatccgcc tggagttccc tgctattgac   1260
gagatggagc agtctattga aaagtttgct tcgctcggcc tggataatca gatcacggag   1320
ctggatatgg gcctgtattc taatgataca gaccactacg aaacgatacc tgaagccatg   1380
ctgatccggc aggctcaccg ctatcgggcg ttgttcgata tgttttcccg acagcaggag   1440
catatcagta atgtgacgat tggggtacg gatgatggaa atacgtggct cagtatgttc   1500
ccgattgccc ggctggataa gccgctgctg ttcgacgaac ggttaaaggc caaatatgcc   1560
tattgggcgc ttgttgaccc gtccaaagta ccgccgctgc cagcggggag caacgaatag   1620
```

<210> SEQ ID NO 4
<211> LENGTH: 539
<212> TYPE: PRT
<213> ORGANISM: Artificial Sequence
<220> FEATURE:
<223> OTHER INFORMATION: SLX-09 protein sequence

```
<400> SEQUENCE: 4

Met Asp Thr Leu Lys Leu Tyr Val Glu Ser Ser Asn Pro Ala Gln Ala
1               5                   10                  15

Tyr Tyr Leu Asp Glu Val Glu Ile Arg Gln Val Ser Glu Thr Pro Thr
            20                  25                  30

Thr Pro Pro Thr Glu Pro Thr Ser Gly Ile Glu Ser Arg Phe Glu Asp
        35                  40                  45

Gly Thr Ala Gln Gly Trp Val Ser Arg Met Gly Thr Glu Thr Val Gln
    50                  55                  60

Val Ser Asn Ala Asp Ala Arg Thr Gly Ser Tyr Ser Leu Leu Thr Thr
65                  70                  75                  80

Gly Arg Gln Gln Thr Tyr Ala Gly Pro Lys Leu Asp Val Thr Ala Thr
                85                  90                  95

Val Gln Lys Gly Ser Arg Tyr Thr Val Ser Ala Trp Val Lys Leu Ala
            100                 105                 110

Pro Gly Glu Gln Gln Pro Ala Lys Val Arg Leu Ser Val Gln Arg Asp
        115                 120                 125

His Gln Gly Glu Ser Thr Tyr Glu Thr Val Val Gly Asn Thr Ala Ile
    130                 135                 140

Thr Thr Gly Gly Trp Thr His Leu Tyr Gly Thr Tyr Thr Leu Ala His
145                 150                 155                 160

Glu Ala Asp Thr Val Ser Met Tyr Leu Glu Thr Pro Glu Gly Thr Ala
                165                 170                 175

Ser Phe Tyr Met Asp Asp Phe Glu Leu Ser Leu Val Pro Pro Leu Ala
            180                 185                 190

Ile Glu Lys Asp Ile Pro Ser Leu His Gly Leu Tyr Gln Gly Gln Phe
        195                 200                 205

Ser Ile Gly Thr Ala Ile Glu Ala Phe Gln Thr Glu Gly Ala Tyr Gly
    210                 215                 220

Glu Leu Val Gln Lys His Phe Asn Ser Val Val Ala Gly Asn Ala Met
225                 230                 235                 240

Lys Pro Ile Ser Leu Gln Pro Ser Glu Gly Gln Phe His Trp Glu Glu
                245                 250                 255

Ala Asp Arg Ile Val Gln Phe Ala Gln Gln His Gly Ile Ala Ile Arg
            260                 265                 270

Phe His Thr Leu Val Trp His Asn Gln Thr Gly Asp Trp Met Phe Lys
        275                 280                 285

Asp Lys Asn Gly Gln Pro Met Thr Pro Thr Ala Glu Asn Lys Lys Leu
    290                 295                 300

Leu Leu Asp Arg Leu Glu Thr His Ile Arg Ala Val Ala Ala Arg Tyr
305                 310                 315                 320

Lys Asn Val Ile Thr Asp Trp Asp Val Val Asn Glu Val Ile Asp Pro
                325                 330                 335

Asp Gln Pro Asp Gly Met Arg Arg Ser Lys Trp Tyr Gln Ile Thr Gly
            340                 345                 350

Thr Asp Tyr Ile Asp Lys Ala Phe Arg Val Thr Arg Glu Ala Ala Gly
        355                 360                 365

Pro Asn Ala Arg Leu Tyr Ile Asn Asp Tyr Asn Thr His Glu Pro Lys
    370                 375                 380

Lys Arg Asp Phe Leu Tyr Asn Leu Val Arg Asp Leu Leu Ala Lys Gly
385                 390                 395                 400

Val Pro Ile Asp Gly Val Gly His Gln Ser His Ile Arg Leu Glu Phe
                405                 410                 415
```

```
Pro Ala Ile Asp Glu Met Glu Gln Ser Ile Glu Lys Phe Ala Ser Leu
                420             425                 430
Gly Leu Asp Asn Gln Ile Thr Glu Leu Asp Met Gly Leu Tyr Ser Asn
            435                 440                 445
Asp Thr Asp His Tyr Glu Thr Ile Pro Glu Ala Met Leu Ile Arg Gln
            450                 455                 460
Ala His Arg Tyr Arg Ala Leu Phe Asp Met Phe Ser Arg Gln Gln Glu
465                 470                 475                 480
His Ile Ser Asn Val Thr Ile Trp Gly Thr Asp Asp Gly Asn Thr Trp
                485                 490                 495
Leu Ser Met Phe Pro Ile Ala Arg Leu Asp Lys Pro Leu Leu Phe Asp
                500                 505                 510
Glu Arg Leu Lys Ala Lys Tyr Ala Tyr Trp Ala Leu Val Asp Pro Ser
            515                 520                 525
Lys Val Pro Pro Leu Pro Ala Gly Ser Asn Glu
    530                 535

<210> SEQ ID NO 5
<211> LENGTH: 30
<212> TYPE: DNA
<213> ORGANISM: Artificial Sequence
<220> FEATURE:
<223> OTHER INFORMATION: SLX-09 sense primer

<400> SEQUENCE: 5
ctcgagatgg atacattgaa gttgtatgtg                                    30

<210> SEQ ID NO 6
<211> LENGTH: 22
<212> TYPE: DNA
<213> ORGANISM: Artificial Sequence
<220> FEATURE:
<223> OTHER INFORMATION: SLX-09 antisense primer

<400> SEQUENCE: 6
ggatccctat tcgttgctcc cc                                            22
```

PAENIBACILLUS SP. HPL-3 STRAIN PRODUCING XYLANASE HAVING HEAT-RESISTANCE, A WIDE RANGE OF OPTIMUM PH AND HIGH ACTIVITY, A NOVEL XYLANASE SEPARATED FROM THE STRAIN, AND A METHOD FOR MASS-PRODUCTION OF THE SAME USING THE TRANSFORMANT ORIGINATED FROM THE STRAIN

BACKGROUND OF THE INVENTION

1. Field of the Invention

The present invention relates to a novel *Paenibacillus* sp. strain producing novel xylanase, a novel xylanase separated from the strain, and a method for mass-production of the same using the transformant of the strain. More precisely, the said novel xylanase exhibits excellent activity of decomposing xylan at high temperature or in a wide range of pH, so that the novel enzyme can be effectively used not only in the fields of feeds, paper and detergent industries, but also in the field of biochemical industry producing bio-fuel, petroleum alternative fuel, performance chemical, or bio-polymer.

2. Description of the Related Art

To keep pace with the changes of international environmental regulations including reduction of carbon dioxide emission, humankind of $21^{st}$ century has the assignment to develop alternative resources of fossil fuel. In preparation of global warming and oil resource depletion, solar energy, wind power, hydropower, atomic power, and biomass have been major targets of research. In the process of biorefinery for the production of bio-fuel and chemical fuel via saccharification of lignocellulosic biomass, it is inevitable to produce the by-product, xylan, that is included in the lignocellulosic biomass by 15-30%. However, it is not possible to use the by-product directly, so most of it are discarded as wastes.

Hydrolysis of xylan has been induced via chemical method so far, which is precisely as follows: sulfuric acid is added to lignocellulosic biomass, followed by decomposing at 130° C. with pressurized steam; leading to the conversion into xylose and xyloologosaccharide. However, in the above process, many impurities are additionally generated by excessive reaction. Therefore, purifying technique is additionally requested. This method has other disadvantages as follows: it not only consumes a massive amount of energy but also requires high priced equipments durable in acid and high temperature condition, and it costs extra money for the treatment of wastes generated during the processes, raising the production cost as well. On the other hand, the biological method for xylan decomposition using xylanase (the enzyme that converts xylan, the major component of hemicellulose, into xylose via saccharification is generally called xylanase) consumes less energy and produces less wastes, compared with the chemical method, suggesting that it has an economical advantage owing to the easy treatment of less wastes.

Xylanase is not only urgently requested in the process of biorefinery (biochemical industry) but also utilized in the process of paper bleaching, for the improvement of feeds efficiency, in the clearing process of fruit beverages, for the production of high quality bread, and in the utilization of agricultural by-products, etc. Xylanase has been produced by using various microorganisms up to date. In particular, alkali-resistant or heat-resistant xylanase was isolated from various bacteria for the use in breaching process of paper industry (Tenkanen, M. et. al., Enzyme. Microb. Technol, 14, 566-574, 1992). Many xylanase producing microorganisms without cellulase activity have been reported, and attempts to reduce cellulose loss in the production of paper have been also reported (Khashin, A. et. al., Appl. Environ. Microbiol, 59, 1725-1730, 1993; Kosugi, A. et. al., J. Bacteriol, 183, 7037-7043, 2001). Successful cases have been reported to improve quality of bread by treating xylanase (Courtin, C. M. et. al., J. Agric. Food. Chem., 47, 1870-1877, 1999), and to introduce β-xylosidase and xylanase genes into yeast that is further used for saccharification of agricultural by-products for a microorganism to use them (La Grange, D. C. et. al., Appl. Environ. Microbiol, 67, 5512-5519, 2001). In the feeds industry, xylanase came into the market as a feed additive enzyme. So, when the cattle eat grain feeds containing the feed additive enzyme, the enzyme is functioning lower viscosity generated by hemicellulose of the intestines of the cattle, indicating that it is helpful to prevent digestive disease in the cattle and to improve feed efficiency (McCracken, K. J. et. al., Br. Poult. Sci, 42, 638-642, 2001).

Among the xylanase producing microorganisms reported so far, *Trichoderma* sp. fungal strains have been largely used whose enzyme productivity is superior than other xylanase producing bacteria but the maximum activity is mainly observed in acidic condition (Tenkanen at al., *Enzyme and Microbial Technology* 14(7):566-574, 1992). Xylanase producing bacteria are exemplified by *Aeromonas* sp., *Bacillus* sp., *Clostridium* sp., *Streptomyces* sp., *Aspergillus* sp, etc. The properties of xylanase depend on the bacteria and various genes able to encode xylanase have also been reported.

Status of domestic and international technology involved in xylanase is as follows. *Trichoderma* sp. C-4 strain producing cellulase was identified by Dr. Jung's research team of Kyung Hee University, Korea, however, higher activity is required for the industrialization (Sul et al., *Appl Microbiol Biotechnol.* 66(1):63-70, 2004). *Cephalosporium* sp. RYM-202 strain producing alkali-resistant xylanase was identified by Dr. Kang's research team of Donghae University, Korea, and its usability in pulp processing is being studied (Kang et al., *Korean Journal of Environmental Biology* 17(2):191-198, 1999). *Bacillus subtilis* DB104/pJHKJ4, the recombinant strain producing *Bacillus* originated endoxylanase, was constructed by Dr. Kim's research team of KAIST, Korea (Kim J H et al., *J. Microbiol. Biotechnol.*, 10(4):551-553, 2000). In Taiwan, a case has been reported that alkali-resistance of xylanase genetically replicated from the anaerobic fungus *Neocallimastix patriciarum* was increased by directed enzyme evolution (Yew-Loom Chen et al., *Can. J. Microbiol.* 47(12):10881094, 2001) and recently *Bacillus firmus*, one of the alkali-resistant strains, has been identified in waste water generated from the pulp processing (Pochih Chang, *Biochemical and Biophysical Research Communications* 319: 1017-1025, 2004). This xylanase demonstrates high activity in the wide pH range of 4~11 and heat-resistance as high as maintaining 70% of the original activity even after 16 hour culture at 62° C. Likewise, various strains have been developed and their functions have been improved via directed evolution in many countries.

Patents in relation to xylanase so far are mainly focused on the method for producing xylanase by using a recombinant strain obtained from *E. coli* or using wild-type strain identified as xylanase producing one (International Patent Publication No. 93/08275, International Patent Publication No. 92/01793, International Patent Publication No. 92/17573, Korean Patent Publication No. 10-0072225, Korean Patent Publication No. 10-02211204, Korean Patent Publication No. 10-0411771). Patents in relation to xylanase as a feed additive so far are as follows: Novel *Streptomyces* sp. WL-2 strain producing xylanase (Korean Patent Publication No. 2001-0111986); Recombinant plasmid containing secretion signal sequence of endoxylanase from *Bacillus subtilis* and expression of foreign proteins using thereof (Korean Patent Publication No. 2000-0034279); and Gene coding xylanase of *Bacillus* sp. AMX-4 strain and recombinant xylanase through transformant thereof (Korean Patent Publication No. 2003-0085679).

Domestic patents in relation to xylanase so far are as follows: Novel *Streptomyces* sp. WL-2 strain producing xylanase (Korean Patent Publication No. 2001-0111986); Recombinant plasmid containing secretion signal sequence of endoxylanase from *Bacillus subtilis* and expression of foreign proteins using thereof (Korean Patent Publication No. 2000-0034279); Gene coding xylanase of *Bacillus* sp. AMX-4 strain and recombinant xylanase through transformant thereof (Korean Patent Publication No. 2003-0085679); and Novel *Paenibacillus* sp. HY-8 strain and xylanase isolated from it (Korean Patent Publication No. 2007-0082329). However, there was no specific explanation about the enzyme activity, neither was reported the cases of using them in domestic industry. Owing to the advanced technology, new methods to polymerize and produce various valuable compounds based on biomass such as high molecular compounds (plastic) have been developed and therefore it is urgently requested to develop xylanase with novel characteristics to match with the above.

For the efficient use of biomass, the development of saccharification process of cellulose using cellulase and the development of saccharification process of hemicellulose using xylanase need to be achieved at the same time. In the enzymatic saccharification process using xylanase, the characteristics of each enzyme required for the process are different according to the pre-treatment method of biomass. For example, in the process of pre-treatment of biomass using acid, acid-resistant saccharifying enzyme is required, while alkali-resistant saccharifying enzyme is required in the process of pre-treatment of biomass using alkali such as in the processes of pulp or paper production. In the meantime, heat-resistant enzyme is required for the simultaneous process of saccharification and fermentation. Most of commercialized xylanases are suitable for acid condition, indicating that novel xylanase demonstrating high activity under alkali condition needs to be developed. It is better to develop such xylanase that shows high activity in both acid and alkali conditions. To use xylanase directly in industry, it is important to secure xylanase gene that is able to maintain high activity under tough conditions such as high temperature and a wide range of pH via screening novel microorganisms and enzyme systems, from which the disadvantages shown in the conventional patents might be overcome.

To avoid those xylanases and those strains producing the same which have already been claimed by other advanced countries, not to infringe intellectual property right, the present inventors tried to develop novel xylanase to meet the domestic and further international need. In the course, the inventors completed this invention by confirming that the xylanase produced from the novel *Paenibacillus* sp. HPL-3 strain demonstrated excellent activity unit (Unit=mM product/mg protein/min), heat-resistance and a wide range of optimum pH, compared with the conventional xylanases, confirmed by solid culture and/or liquid culture enzyme activity measurement method.

SUMMARY OF THE INVENTION

It is an object of the present invention to provide xylanase having high activity at high temperature and in a wide range of pH.

It is another object of the present invention to provide a strain producing the said xylanase.

It is further an object of the present invention to provide a polynucleotide encoding the said xylanase.

It is also an object of the present invention to provide a recombinant expression vector operably linked to the said polynucleotide.

It is also an object of the present invention to provide a transformant prepared by introducing the said recombinant expression vector into host cells.

It is also an object of the present invention to provide a production method of xylanase containing the step of obtaining crude enzyme solution by centrifugation after culturing the strain or the transformant above in a medium.

It is also an object of the present invention to provide a xylan decomposer comprising the said xylanase, the said strain, or the said transformant.

It is also an object of the present invention to provide a composition for processing food xylan comprising the said xylanase.

It is also an object of the present invention to provide a feed additive comprising the said xylanase.

It is also an object of the present invention to provide a composition for papermaking process comprising the said xylanase.

It is also an object of the present invention to provides a method for decomposing xylan containing the step of adding the said xylanase, the said strain, or the said transformant to lignocellulosic biomass or xylan containing solution.

It is also an object of the present invention to provide a preparation method of feeds containing the step of adding the said xylanase, the said strain, or the said transformant to animal feed materials.

It is also an object of the present invention to provide the said xylanase, the said strain, or the said transformant for the use as a xylan decomposer.

It is also an object of the present invention to provide the said xylanase for the use as a composition for processing food xylan.

It is also an object of the present invention to provide the xylanase for the use as a feed additive.

In addition, it is an object of the present invention to provide the xylanase for the use as a composition for papermaking process.

To achieve the above objects, the present invention provide the xylanase having the characteristics of (a)~(d):

(a) molecular weight: approximately 65 KDa on SDS-PAGE;

(b) maximum activity in the range of pH 5~pH 11;

(c) maximum activity at the temperature of 50~60° C.; and (d) xylose production at 50° C., pH 5~pH 11: at least 95 unit/minmg; and xylose production at 60° C., pH 6~pH 9: at least 100 unit/mining.

The present invention also provides a strain producing the said xylanase.

The present invention also provides a polynucleotide encoding the said xylanase.

The present invention also provides a recombinant expression vector operably linked to the said polynucleotide.

The present invention also provides a transformant prepared by introducing the said recombinant expression vector into host cells.

The present invention also provides a production method of xylanase containing the step of obtaining crude enzyme solution by centrifugation after culturing the strain or the transformant above in a medium.

The present invention also provides a xylan decomposer comprising the said xylanase, the said strain, or the said transformant.

The present invention also provides a composition for processing food xylan comprising the said xylanase.

The present invention also provides a feed additive comprising the said xylanase.

The present invention also provides a composition for papermaking process comprising the said xylanase.

The present invention also provides a method for decomposing xylan containing the step of adding the said xylanase, the said strain, or the said transformant to lignocellulosic biomass or xylan containing solution.

The present invention also provides a preparation method of feeds containing the step of adding the said xylanase, the said strain, or the said transformant to animal feed materials.

The present invention also provides the said xylanase, the said strain, or the said transformant for the use as a xylan decomposer.

The present invention also provides the said xylanase for the use as a composition for processing food xylan.

The present invention also provides the xylanase for the use as a feed additive.

In addition, The present invention provides the xylanase for the use as a composition for papermaking process.

Advantageous Effect

As explained hereinbefore, the xylanase separated from *Paenibacillus* sp. HPL-3, the novel strain of the present invention, has excellent heat-resistance at 60° C. and demonstrates excellent xylan decomposing activity in a wide range of pH (4~11), so that this enzyme can be effectively used not only in the fields of feed, paper and detergent industries, but also in the saccharification process of lignocellulosic biomass for the production of raw materials of petroleum alternative material, performance chemical, and bio-polymer.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
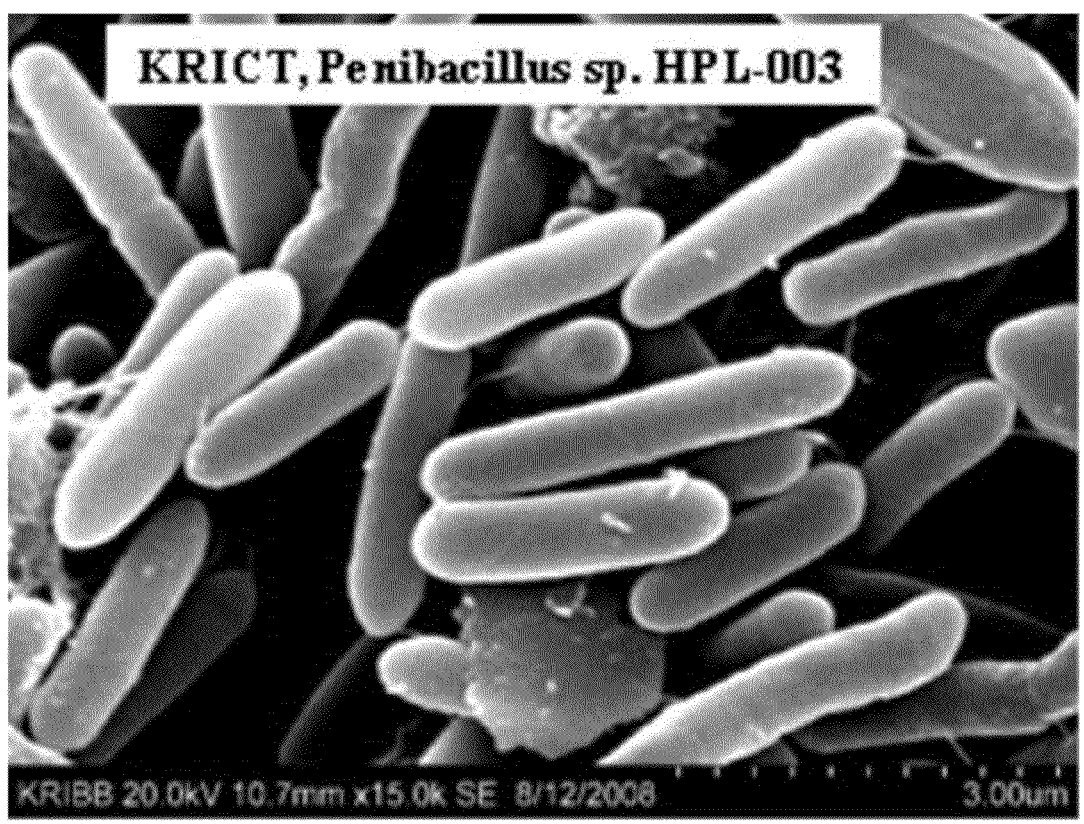
FIG. 1 is a electron micrograph illustrating the selected strain.

Hereinafter, the present invention is described in detail.

The present invention provide the xylanase having the characteristics of (a)~(d):

(a) molecular weight: approximately 65 KDa on SDS-PAGE;
(b) maximum activity in the range of pH 5~pH 11;
(c) maximum activity at the temperature of 50~60° C.; and
(d) xylose production at 50° C., pH 5~pH 11: at least 95 unit/min mg; and xylose production at 60° C., pH 6~pH 9: at least 100 unit/mining.

The amino acid sequence of the xylanase of the present invention preferably contains one of the following sequences, but not always limited thereto:

a) the amino acid sequence represented by SEQ. ID. NO: 4;
b) the amino acid sequence having at least 70% homology, preferably at least 80%, and more preferably at least 90% homology with the amino acid sequence represented by SEQ. ID. NO: 4;
c) the amino acid sequence encoded by the nucleotide sequence represented by SEQ. ID. NO: 3;
d) the amino acid sequence of the protein composed of the modified amino acid sequence having substitution, deletion, insertion, and/or addition of at least one of amino acids of the sequence represented by SEQ. ID. NO: 4, which is also identical in its function to the protein containing the amino acid sequence represented by SEQ. ID. NO: 4; and,
e) the amino acid sequence encoded by DNA hybridized with the DNA containing the nucleotide sequence represented by SEQ. ID. NO: 3 in the strict condition, which is identical in its function to the protein containing the amino acid sequence represented by SEQ. ID. NO: 3.

The said 'strict condition' is determined in the phase of washing after hybridization. One of the strict conditions is exemplified as follows: washing with 6± SSC, 0.5% SDS at room temperature for 15 minutes, then washing with 2± SSC, 0.5% SDS at 45° C. for 30 minutes, and then washing with 0.2± SSC, 0.5% SDS at 50° C. for 30 minutes twice. More preferable strict condition herein means washing at a higher temperature. That is, washing is performed by the same manner as described above only except that the last washing is performed with 0.2± SSC, 0.5% SDS at 60° C. for 30 minutes twice. Another example of the strict condition of the present invention is set with modification of the above washing process, that is the last two washings are performed with 0.1± SSC, 0.1% SDS at 65° C. Whoever in this field can set up and adjust the conditions to satisfy the strict conditions.

The xylanase of the present invention demonstrates maximum activity in the pH range of 5~11, preferably in the pH range of 6~10, and more preferably in the pH range of 6~9, at 50~60° C., but not always limited thereto.

In a preferred embodiment of the present invention, the strain having excellent xylan decomposing activity was collected from the soil containing waste wood residue left after mushroom cultivation in halfway up the mountain Gara located in Dadae-ri, Nambu-myeon, Geoje-si, Gyeongsang-nam-do, Korea.

In a preferred embodiment of the present invention, gDNA library was constructed to separate a gene encoding the enzyme protein having xylanase activity from the said strain, and then xylanase activity was examined. From the experiment, one clone was selected (see FIG. 2), and then nucleotide sequence of the inserted DNA fragment was analyzed. As a result, the size of the DNA fragment was 6,956 bp (SEQ. ID. NO: 2) and 11 ORFs were included in the sequence range of 100 or more amino acids (see FIG. 3). The present inventors investigated homology of those ORF proteins encoded by the gene. Then, *E. coli* was transfected with ORFS (1620 bp, 539 aa) showing 48% homology with endo-1,4-beta-xylanase (GenBank Accession No: YP_001817989), and xylanase activity was investigated. As a result, excellent xylanase activity was confirmed. Nucleotide sequence of target DNA fragment of the transformant was also investigated, and as a result ORF of the novel xylanase gene having the nucleotide sequence represented by SEQ. ID. NO: 3 was confirmed.

In a preferred embodiment of the present invention, the transformant over-expressing xylanase was constructed in order to produce the novel xylanase having the amino acid sequence represented by SEQ. ID. NO: 4 in a large scale. Enzyme activity of the novel xylanase with 65 kD (see FIG. 4) which was produced, separated, and purified from the said transformant *E. coli* was investigated. As a result, maximum activity was observed at 50~60° C., in pH range of 4~11 (see FIGS. 5 and 6). Even though the activity was inhibited by 74%, 28%, 12%, and 46%, respectively by 1 mM of $Cu^{+2}$, $Zn^{+2}$, $Fe^{+2}$, and EDTA, among various heavy metal sources, the enzyme activity was hardly affected at the concentration of 100 HM or rather increased by them (see Table 1). Enzyme kinetics was also investigated. As a result, Km, presenting substrate affinity, was 0.2 (see FIG. 7). Hydrolyzed products were largely xylo-oligomer.

From the results of sequencing and activity analysis, it was confirmed that the xylanase produced from the strain identified in this invention was novel one that was different from the conventional xylanase.

The present invention also provides a strain producing the said xylanase.

The said strain can be prokaryotic cells including *E. coli*, or eukaryotic cells including yeast, animal cells and insect cells, but not always limited thereto. The said strain producing xylanase is preferably *Paenibacillus* sp. HPL-3 deposited under the Accession No. of KCTC11987BP, but not always limited thereto, and any strain that is able to produce xylanase can be included in this invention.

In a preferred embodiment of the present invention, the strain having excellent xylan decomposing activity was collected from the soil containing waste wood residue left after mushroom cultivation in halfway up the mountain Gara located in Dadae-ri, Nambu-myeon, Geoje-si, Gyeongsang-nam-do, Korea. The collected strain was identified as a Gram-positive, rod type, non-motile *bacillus* without flagellum. The cell size was 1.1 μm and the cell length was 2.5~4 μm (see FIG. 1). The strain had 16S rRNA represented by SEQ. ID. NO: 1. From the rRNA homology analysis, it was confirmed that the strain had 95.0% homology with *Paenibacillus* sp. CSH12-5 (GenBank Accession No. EF694701) and 95.7% homology with *Paenibacillus* daejeonensis(T) (GenBank Accession No. AM141; AF391124). Since no higher homology with any other strain was confirmed, the strain of the present invention was named *Paenibacillus* sp. HPL-3, which was deposited at Korean Research Institute of Bioscience and Biotechnology in Jul. 20, 2011 under the Accession No. KCTC1198BP.

The present invention also provides a polynucleotide encoding the said xylanase.

The polynucleotide encoding the xylanase of the present invention preferably contains one of the following sequences, but not always limited thereto:

a) the nucleotide sequence represented by SEQ. ID. NO: 3;

b) the nucleotide sequence having at least 70% homology, preferably at least 80%, and more preferably at least 90% homology with the nucleotide sequence represented by SEQ. ID. NO: 3;

c) the nucleotide sequence encoding the amino acid sequence represented by SEQ. ID. NO: 4;

d) the nucleotide sequence encoding the amino acid sequence of the protein with substitution, deletion, insertion, and/or addition of at least one of amino acids of the sequence represented by SEQ. ID. NO: 4, which is also identical in its function to the protein containing the amino acid sequence represented by SEQ. ID. NO: 4; and, e) the nucleotide sequence comprising DNA sequence to be hybridized with DNA containing the nucleotide sequence represented by SEQ. ID. NO: 3 under the strict condition and encoding the protein having the same function as the protein comprising the amino acid sequence represented by SEQ. ID. NO: 4.

The present invention also provides a recombinant expression vector operably linked to the said polynucleotide.

In this invention, the nucleotide sequence of the novel gene encoding the xylanase separated from *Paenibacillus* sp. HPL-3 strain was identified, so that a recombinant vector containing the said gene can be constructed by the conventional method known to those in the art. The recombinant vector of the present invention can be a commercialized one, but not always limited thereto, and can be constructed by the conventional method known to those in the art.

The present invention also provides a transformant prepared by introducing the said recombinant expression vector into host cells.

The host cells usable in this invention are not limited, but preferably selected from the group consisting of prokaryotic cells including *E. coli* and bacteria, and eukaryotic cells including yeast, animal cells and insect cells, and more preferably *E. coli*, but not always limited thereto.

The present invention also provides a production method of xylanase containing the step of obtaining crude enzyme solution by centrifugation after culturing the strain or the transformant above in a medium.

The production method of the present invention can additionally include the step of purifying xylanase from the obtained crude enzyme solution.

In the above method, the medium is preferably selected among commercialized media well-known to those in the art that is considered to be appropriate for the culture of *Paenibacillus* sp. HPL-3 (KCTC11987BP) or the transformant of the present invention.

To simplify the purification process and to increase purification efficiency, the present inventors used a specific resin binding vector for column-chromatography for the construction of the transformant. It is preferred to select and separate the enzyme linked to resin in the course of purification. For the strict condition herein, glutathione binding vector, calmodulin binding vector, and maltose binding vector can be used and resin for column filling is determined by considering the vector used. In this invention, the results obtained by using glutathione binding vector and resin are presented, but the invention is not limited thereto.

The present invention also provides a xylan decomposer comprising the said xylanase, the said strain, or the said transformant.

The xylan decomposer of the present invention can be not only the xylanase produced in the strain or the transformant of the invention but also the strain or the transformant itself.

The present invention also provides a composition for processing food xylan comprising the said xylanase.

The present invention also provides a feed additive comprising the said xylanase.

The present invention also provides a composition for papermaking process comprising the said xylanase.

The composition or the feed additive of the present invention can include, in addition to the xylanase, one or more effective ingredients having the same or similar function to the xylanase. The preferable concentration of the xylanase of the present invention is 1~90% by the total composition or feed additive, but not always limited thereto.

Unlike the conventional xylanase, the xylanase of the present invention demonstrates excellent activity in a wide range of pH (5~11) and temperature (50~60° C.) (see FIGS. 5 and 6). Therefore, the xylanase of the present invention can be used as the novel xylanase having high activity in the wide pH range and heat-resistance.

The use of xylanase in the enzyme market is largely divided into food industry, feed industry, and technology field (Bedford and Morgana, World's Poultry Science Journal 52:61-68, 1996). In food industry (fruit and vegetable production, brewing and liquor production, bakery and confectionery), xylanase has been used to improve quality of the product by softening raw materials, improving purification efficiency, reducing viscosity, and increasing extraction/filtration efficiency. In feed industry, xylanase has been used to reduce non-starch carbohydrates in feed for pig, poultry and ruminants, to improve intestinal viscosity, and to increase digestibility of protein and starch (Kuhad and Singh, Crit. Rev. Biotechnol. 13, 151-172, 1993). In addition, in the field of technology, xylanase has been used in papermaking process, precisely for biological whitening, reduction of chlorine decay, saving energy through simplifying mechanical papermaking process, separation of starch and gluten, production of renewable fuel (bio-ethanol), and production of chemical raw materials.

Therefore, it is well understood by those in the art that the novel xylanase of the present invention can be effectively used for the decomposition of xylanase industrially used in papermaking and paper recycling, and in feed and food industry to improve quality of the products. The composition of the present invention can be formulated by the conventional method known to those in the art.

The present invention also provides a method for decomposing xylan containing the step of adding the said xylanase, the said strain, or the said transformant to lignocellulosic biomass or xylan containing solution.

In the above method, the amount of the strain, the transformant, or the novel xylanase produced by the strain or the transformant can be adjusted by those in the art.

The present invention also provides a preparation method of feeds containing the step of adding the said xylanase, the said strain, or the said transformant to animal feed materials.

In the above method, the amount of the strain, the transformant, or the novel xylanase produced by the strain or the transformant can be adjusted by those in the art.

The present invention also provides the said xylanase, the said strain, or the said transformant for the use as a xylan decomposer.

The xylan decomposer of the present invention can be not only the xylanase produced in the strain or the transformant of the invention but also the strain or the transformant itself.

The present invention also provides the said xylanase for the use as a composition for processing food xylan.

The present invention also provides the xylanase for the use as a feed additive.

In addition, The present invention provides the xylanase for the use as a composition for papermaking process.

The said xylanase preferably has the characteristics of (a)~(d), but not always limited thereto:
  (a) molecular weight: approximately 65 KDa on SDS-PAGE;
  (b) maximum activity in the range of pH 5~pH 11;
  (c) maximum activity at the temperature of 50~60° C.; and
  (d) xylose production at 50° C., pH 5~pH 11: at least 95 unit/min mg; and xylose production at 60° C., pH 6~pH 9: at least 100 unit/min mg.

The amino acid sequence of the said xylanase preferably contains one of the below sequences, but not always limited thereto:
  a) the amino acid sequence represented by SEQ. ID. NO: 4;
  b) the amino acid sequence having at least 70% homology, preferably at least 80%, and more preferably at least 90% homology with the amino acid sequence represented by SEQ. ID. NO: 4;
  c) the amino acid sequence encoded by the nucleotide sequence represented by SEQ. ID. NO: 3;
  d) the amino acid sequence of the protein composed of the modified amino acid sequence having substitution, deletion, insertion, and/or addition of at least one of amino acids of the sequence represented by SEQ. ID. NO: 4, which is also identical in its function to the protein containing the amino acid sequence represented by SEQ. ID. NO: 4; and,
  e) the amino acid sequence encoded by DNA hybridized with the DNA containing the nucleotide sequence represented by SEQ. ID. NO: 3 in the strict condition, which is identical in its function to the protein containing the amino acid sequence represented by SEQ. ID. NO: 3.

Unlike the conventional xylanase, the xylanase of the present invention demonstrates excellent activity in a wide range of pH (5~11) and temperature (50~60° C.) (see FIGS. 5 and 6). Therefore, the xylanase of the present invention can be used as the novel xylanase having high activity in the wide pH range and heat-resistance for the composition for processing food xylan, for feed additive, or for papermaking process.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Isolation and Selection of Strain

<1-1> Isolation of Strain

The strain of the present invention was collected from the soil containing waste wood residue left after mushroom cultivation in halfway up the mountain Gara located in Dadae-ri, Nambu-myeon, Geoje-si, Gyeongsangnam-do, Korea. Soil sample was collected from 2~5 cm under the surface layer, which was dried over wind and filtered with 2 mm sieve. The filtered soil sample (30 g) was loaded in 270 ml of sterilized saline (NaCl 8.0 g/l), followed by shaking in a shaking incubator (37° C., 200 rpm) for 20 minutes. The soil sample stood at room temperature for 30 minutes to precipitate big soil particles and impurities on the bottom. The supernatant was transferred in a sterilized container, leading to the preparation of the first diluted solution. The first diluted solution was stirred well and then 10 ml of the solution was taken and loaded in 90 ml of saline to prepare the second diluted solution (100 ml). The second diluted solution was stirred well and then 10 ml of the solution was taken again and loaded in 90 ml of saline to prepare the third diluted solution (100 ml). Then, the fourth, fifth and sixth diluted solutions were prepared by the same manner as described above. The 3rd, 4th, 5th, and 6th diluted solutions were distributed in TSA (Tryptic Soy Agar, Difco Co.) medium for strain separation, three times by 0.25 ml at a time. The diluted solutions were smeared evenly on the medium and culture was performed in a 37° C. bench-type incubator for 2 days. Then, the formed microorganism colonies were selected. The selected colonies were separated by shape, size, color, and other relevant factors. The separated colonies were sub-cultured in TSA medium, to isolate pure strains which were stored at −70° C. for being used as the mother strain.

<1-2> Selection of Strain

For the selection of active strain showing xylanase activity among the isolated pure strains, soft agar double medium was prepared by adding birch xylan (Fluka Bio Chemika. Co.) to TSA medium by 0.5~1.0%, to which the isolated strains were inoculated. After overnight culture, those strains forming translucent zone (halo) around the cultured colony and active clones were selected by Congo-red staining method (Theater R M, P J. Wood. *Appl Environ Microbiol* 43, 777-780, 1982; Beguin P. *Analytical Biochemistry,* 131(2):333-336, 1983). Xylan decomposing activity of the selected strain was measured again to confirm reproducibility. Among those strains, the strain demonstrating most excellent xylan decomposing activity was selected finally as the microorganism producing xylanase.

Example 2

Identification of Strain

The present inventors cultured the strain producing xylanase demonstrating the highest activity, isolated in Example 1, at 30° C., and then performed Gram staining and spore staining. As a result, the strain of the present invention was confirmed to be Gram-positive *bacillus* forming spores. The morphology of the strains was observed under electron microscope. As shown in FIG. 1, the strain was identified as a rod type, non-motile *bacillus* without flagellum. The cell size was 1.1 µm and the cell length was 2.5~4 µm. From analysis of 16S rRNA nucleotide sequence of the strain, 1234 bp rDNA represented by SEQ. ID. NO: 1 was obtained, followed by screening with GenBank database. As a result, it was confirmed that the strain had 96.4% homology with *Pantoea agglomerans* ZFJ-15 (GenBank Accession No. EU931554) and 96.3% homology with *Paenibacillus* sp. WPCB158 (GenBank Accession No. FJ006910). Since no higher homology was confirmed, the strain of the present invention was named *Paenibacillus* sp. HPL-3, which was deposited at Korean Research Institute of Bioscience and Biotechnology in Jul. 20, 2011 under the Accession No. of KCTC1198BP.

Example 3

Separation of Novel Xylanase

<3-1> Construction of *Paenibacillus* Strain Gene Library and Activity Test

To separate the gene encoding the enzyme protein having xylanase activity from the *Paenibacillus* sp. HPL-3 strain separated and identified in Example 1 and Example 2, genome DNA was first extracted to construct gDNA library containing gene fragments less than 5 kb. To construct the library, the extracted DNA was fragmented into 1~6 kb sized fragments by random digestion, followed by electrophoresis on agarose gel. The fragments were sorted by size and those DNA fragments having approximately 5 kb size were selected. The fragments were inserted in pCB31 plasmid vector, with which *E. coli* DH10B was transfected. Xylanase activity was investigated with 1,248 clones of the constructed library in solid or liquid condition.

<3-2> Xylanase Activity Test

Figure 2:
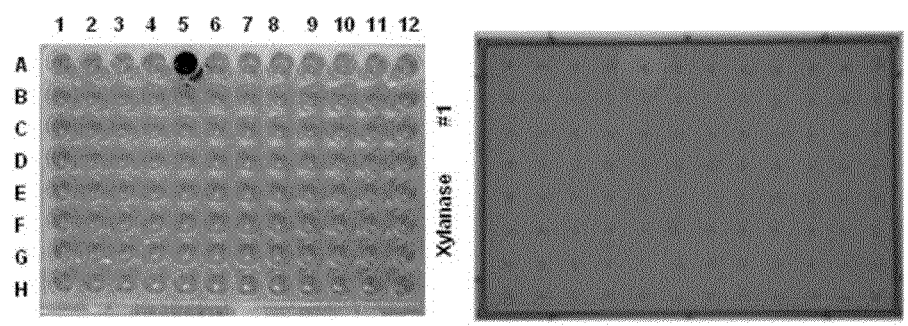
FIG. 2 is a diagram illustrating the selection of active clones from 1,248 gDNA library.
Figure 3:
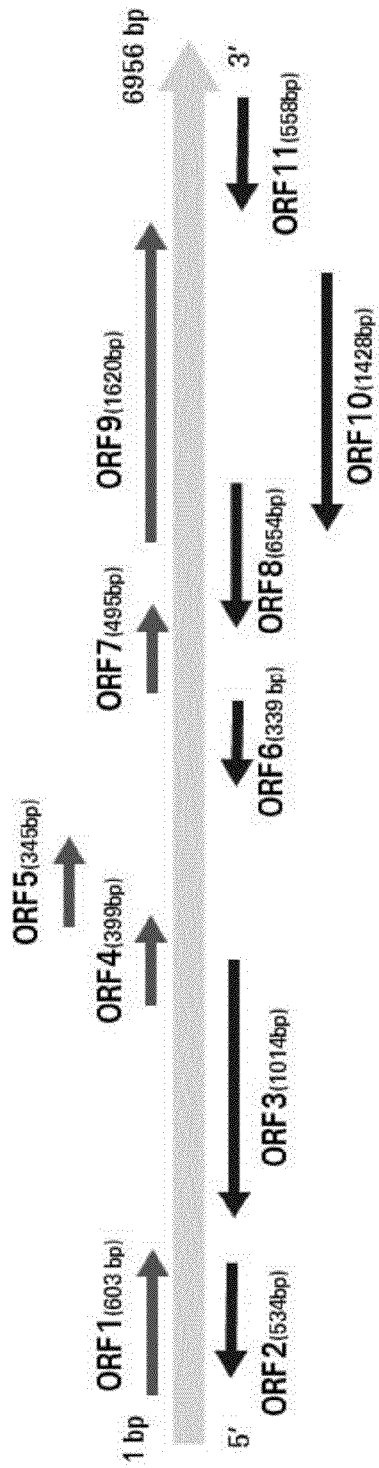
FIG. 3 is a diagram illustrating the results of ORF analysis and homology analysis among ORF amino acids.

The measurement of xylanase activity (xylan decomposing activity) of the isolated strain, active clone, transformant, and isolated/purified enzyme was performed by either or both of the following two methods. The first method was enzyme activity measuring method using solid culture. Particularly, soft agar double medium was prepared by adding birch xylan (Fluka Bio Chemika. Co.) to LB medium by 0.5~1.0%, to which the strain was inoculated, followed by culture for overnight. On the next day, the strain and active clone forming translucent zone (halo) around the cultured colony were selected by Congo-red staining. The second method was enzyme activity measuring method using liquid culture, that is DNS (3,5-dinitrosalicylic acid) quantitative method (Miller G. L. *Anal Chem* 31, 426-428, 1959). Particularly, 50 µl of substrate solution (50 mM Tris-HCl containing birch xylan by 2%, pH 7.0) was added to 50 µl of enzyme solution, followed by reaction at 50° C. for 20 minutes. 200 µl of DNS solution was added thereto, followed by further reaction at 90° C. for 5 minutes. Then, $OD_{540}$ was measured. 1 unit of the enzyme was defined as the enzyme activity of 1 mg xylanase to produce 1 µmol of reducing sugar (xylose) per 1 minute. One clone showing the best activity, GM3-SLX1, was selected by liquid culture and solid culture activity test (FIG. 2).

<3-3> Selection of Xylanase Active Clone and Gene Assay

Sequencing of the DNA fragment inserted in the clone selected in Example <3-2> was performed. As a result, the size of the DNA fragment inserted in the plasmid was 6,956 bp (SEQ. ID. NO: 2). ORF (Open Reading Frame) was also investigated by using NCBI Blast P or Blast N program (//www.ncbi.nlm.nih.gov/). Among the ORFS analyzed above, 11 ORFS having the size of at least 100 amino acids were named as follows: SLX-O1, SLX-O2, SLX-O3, SLX-O4, SLX-O5, SLX-O6, SLX-O7, SLX-O8, SLX-O9, SLX-O10, and SLX-O11. Among the ORFs, SLX-O9 (SEQ. ID. NO: 3) showing 48% homology with endo-1,4-beta-xylanase (AJ006646) was selected as a target. Based on nucleotide sequence of the target, the primer having the addition of XhoI and BamHI sites was constructed, followed by amplification by PCR. Then, the amplified primer was inserted in pGEM-T-Easy vector (Promega) to construct a recombinant plasmid.

Particularly, 1 ng of GM3-SLX1 template plasmid was mixed with the primer set (10 pmol) composed of the forward primer represented by SEQ. ID. NO: 5 (5'-CTCGAGATG-GATACATTGAAGTTGTATGTG-3') and the reverse primer represented by SEQ. ID. NO: 6 (5'-GGATCCCTATTCGT-TGCTCCCC-3'), followed by PCR using PCR Premix (GenetBio) as follows: predenaturation at 94° C. for 5 minutes, denaturation at 94° C. for 30 seconds, annealing at 55° C. for 30 seconds, extension at 72° C. for 1 minute, 30 cycles from denaturation to extension, and final extension at 72° C. for 7 minutes. Then reaction was terminated at 4° C. The PCR amplified product was purified by using GENCLEAN II Kit (Q-Biogene), and a recombinant DNA was constructed with pGEM-T-easy vector using T4 ligase (RBC). *E. coli* transformant was prepared by transfecting *E. coli* JM109 with the recombinant plasmid. The transformant was cultured in LB liquid medium, and then, plasmid DNA was extracted by using HiYield™ Plasmid Mini Kit (RBC). The extracted plasmid DNA was digested with XhoI (NEB) and BamHI (NEB), followed by electrophoresis to confirm the insertion of the target DNA fragment. Xylanase activity of the said transformant was investigated in the liquid phase as explained in Example <3-2>. As a result, xylanase activity was observed therein.

Nucleotide sequence of the target DNA fragment of the transformant was investigated and as a result ORF of the novel xylanase gene represented by SEQ. ID. NO: 4 was confirmed.

<3-4> Construction of Transformant Over-Expressing Xylanase (pIVEX-GST-PX3)

Figure 4:
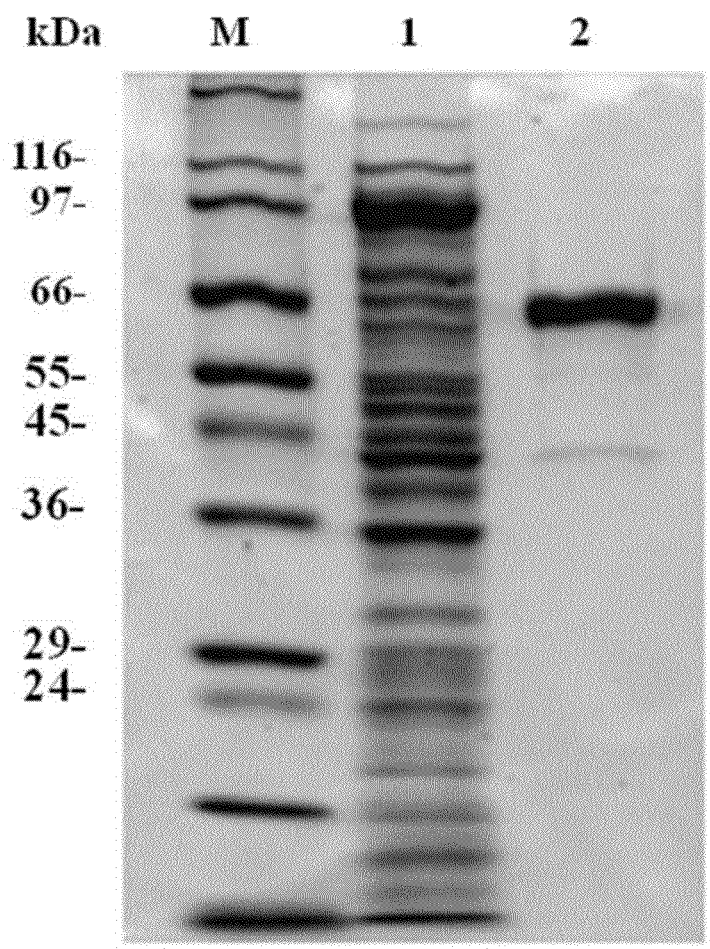
FIG. 4 is a diagram illustrating the activity of the xylanase separated and purified from the transformant.

To construct a transformant over-expressing the novel xylanase, PCR was performed using GM3-SLX1 plasmid as a template with the primer set composed of the sequence represented by SEQ. ID. NO: 5 and the sequence represented by SEQ. ID. NO: 6. PCR reaction mixture and the reaction condition were same as described in Example <3-2>. The amplified product was purified and digested with XhoI (NEB) and BamHI (NEB), which was inserted in pIVEX-GST (Roche), the protein over-expressing vector, to construct the recombinant over-expression plasmid. *E. coli* transformant over-expressing xylanase was prepared by transfecting *E. coli* BL21v (RBC) with the recombinant plasmid. The constructed *E. coli* transformant over-expressing xylanase was cultured and plasmid DNA was extracted. The extracted plasmid DNA was digested with the said restriction enzymes, followed by electrophoresis to confirm that the target DNA and the vector were successfully recombinated. The identified strain was cultured in LB liquid medium (supplemented with 100 ampicillin/ml) for 18 hours (37° C., 250 rpm, A600=1.0) and inoculated in fresh LB liquid medium. When $OD_{600}$ reached 0.4~0.6, the medium was treated with 1 mM of IPTG, followed by further culture for 3 hours. Then, cells were collected, resuspended and sonicated. The sonicated cell suspension was centrifuged at 10,000 g to separate supernatant and precipitate. The target protein over-expressed in the supernatant was confirmed. Molecular weight of the target protein was approximately 65 kD, which was confirmed by SDS-PAGE (FIG. 4).

<3-5> Condition for Xylanase Activity Expression

In this example, pH, temperature, and metal ion-dependent activity of xylanase over-expressed and isolated from the *E. coli* transformant over-expressing the novel xylanase constructed in Example <3-4> was investigated by the same manner as described in example 3-2. pH of the reaction solution was regulated to pH 4~5 with citric acid buffer, to pH 6~8 with phosphate buffer, to pH 7~9 with Tris/HCl buffer, and to pH 9~11 with glycine/NaOH buffer. To investigate the effect of metal ions on xylanase activity, $CaCl_2$, MgCl2, $MgCl_2$, $CuCl_2$, $ZnCl_2$, and $FeCl_3$ were added by 1 mM each. It was further investigated how other salts such as NaCl, LiCl, KCl, $NH_4Cl$, EDTA, $CsCl_2$, 2-ME (2-Mercaptoethanol), DTT (Dithiothreitol), PMSF (Penylmethylsulfonyl fluoride), acetate, and furfural could affect xylanase activity.

Figure 5:
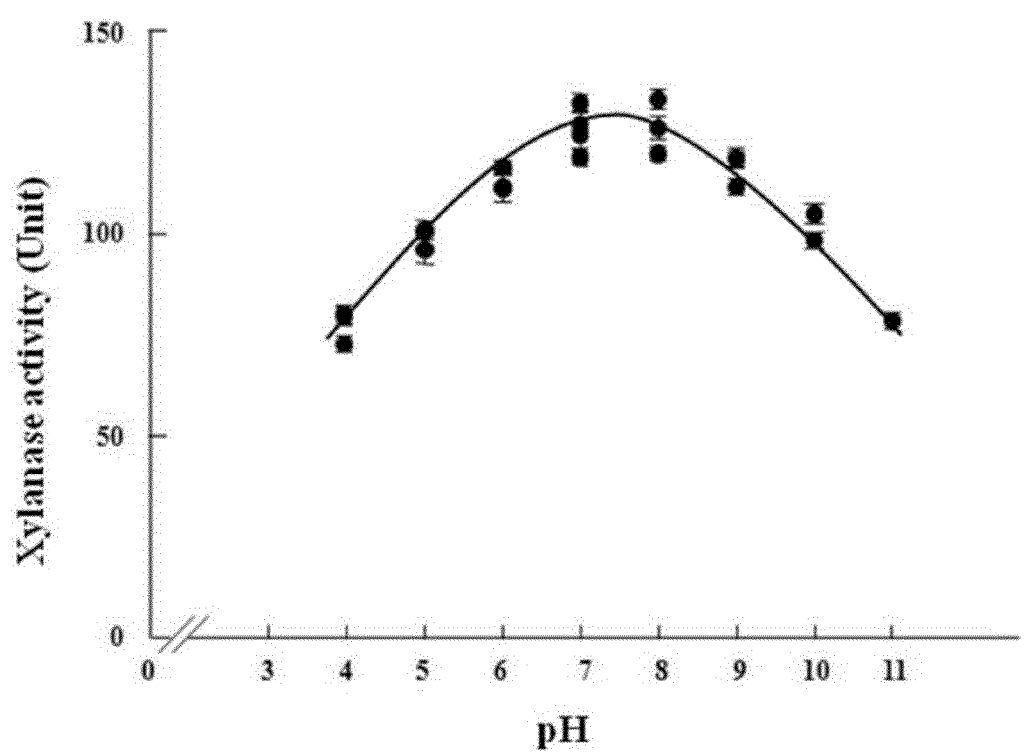
FIG. 5 is a graph illustrating the optimum pH range of the xylanase.
Figure 6:
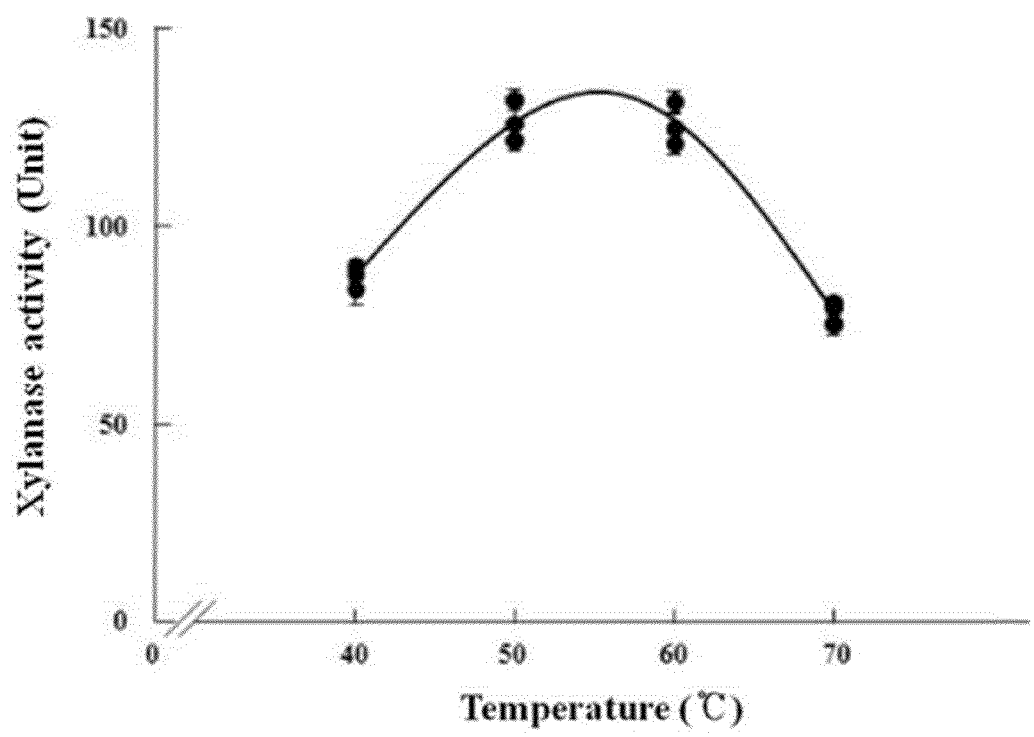
FIG. 6 is a graph illustrating the optimum temperature range of the xylanase.

As a result, the novel xylanase demonstrated the maximum activity at the pH range of 4~11 as shown in FIG. 5, and at the temperature range of 50~60° C., as shown in FIG. 6. As shown in Table 1, xylanase activity was inhibited by 74%, 28%, 12%, and 46% respectively by 1 mM of such heavy metal or additive as $Cu^{+2}$, $Zn^{+2}$, $Fe^{+2}$, and EDTA.

TABLE 1

| Additive | Relative activity according to conc. of additive (%) 1 mM |
|---|---|
| Negative Control | 100 |
| NaCl | 105 |
| LiCl | 101 |
| KCl | 101 |
| NH4Cl | 99 |
| CaCl₂ | 102 |

TABLE 1-continued

| Additive | Relative activity according to conc. of additive (%) 1 mM |
|---|---|
| MgCl₂ | 93 |
| MnCl₂ | 98 |
| CsCl₂ | 97 |
| CuSO₄ | 26 |
| ZnSO₄ | 72 |
| FeCl₃ | 88 |
| EDTA | 54 |
| 2-ME | 89 |
| DTT | 95 |
| PMSF | 95 |
| Acetate | 101 |
| Furfural | 98 |

Example 4

Mass-Production of the Novel Xylanase

*E. coli* BL21-Gold (DE) (Stratagene, USA) was transfected with pIVEX GST-xylanase recombinant vector (Bioprogen Co., Ltd., Korea) containing the gene (SEQ. ID. NO: 3) encoding the novel xylanase represented by SEQ. ID. NO: 4, which was inoculated in liquid medium (LB 25 g/L) supplemented with ampicillin (50 μg/ml), followed by shaking culture at 37° C. at 150 rpm until $OD_{603}$ reached 0.4~0.6. To induce the expression of the target protein in *E. coli* cells, IPTG (isopropyl-D-thiogalactoside) was added to the suspension at the concentration of 1 mM, followed by further culture for 3 hours. The culture solution was centrifuged at 10,000 rpm for 10 minutes and the recovered precipitate was washed with PBS twice. The washed precipitate was re-suspended in PBS and then cell were lysed by using a ultrasonicator (Cosmo Bio Co., LTD). Centrifugation was performed (12,000 rpm, 10 minutes) to obtain supernatant. To isolate xylanase from the supernatant, glutathione S-transferase column (GST binding resin column, Novagen) was used. For xylanase separation, the obtained supernatant was filled in glutathione S-transferase column (GST binding resin column, Novagen) equilibrated with washing buffer (50 mM Tris-HCl, 100 mM NaCl; pH 7.0), followed by treatment of factor Xa protease (NEB) and separation using washing buffer (50 mM Tris-HCl, 100 mM NaCl; pH 7.0). The enzyme activity of xylanase in each sample recovered from the purification stage was investigated. The purification of active fraction showing the enzyme activity was confirmed by SDS-PAGE. Protein content was measured by using Bradford method (Bradford, Sigma Aldrich), and BSA (bovine serum albumin) was used as the standard protein.

As a result, it was confirmed that xylanase was mass-produced easily by glutathione resin column chromatography. Considering the condition of xylanase conjugated onto the resin, it was confirmed that xylanase activity was not changed. Therefore, the novel xylanase could be used for high efficiency conversion process via enzyme immobilization method. The enzyme purified by the above method demonstrated at least 5 times higher activity than before purification. The enzyme activity at 50° C. was 97.37, 124.19, 122.21, 124.61, 122.95, 103.27, and 96.08 units, respectively at pH 5.0, pH 6.0, pH 7.0, pH 8.0, pH 9.0, pH 10.0. and pH 11.0, suggesting that the enzyme activity was guaranteed in a wide range of pH. In the meantime, the enzyme activity at 60° C. was 26.93, 105.19, 123.56, 120.95, 112.25, 29.89, and 22.76 units (μM of xylose produced by 1 mg of enzyme per 1 minute), respectively at pH 5.0, pH 6.0, pH 7.0, pH 8.0. pH 9.0, pH 10.0, and pH 11.0, suggesting that the enzyme had excellent heat-resistance and excellent activity.

Example 5

Characteristics of the Mass-Produced Noble Xylanase

To investigate the characteristics of the enzyme, the purified xylanase was loaded in a test tube, to which 50 mM Tris-HCl (pH 7.0) buffer containing birch xylan at different concentrations was added. The mixture was reacted at 50° C. for 20 minutes to investigate enzymatic reaction rate (Lineweaver-Burk).

Figure 7:
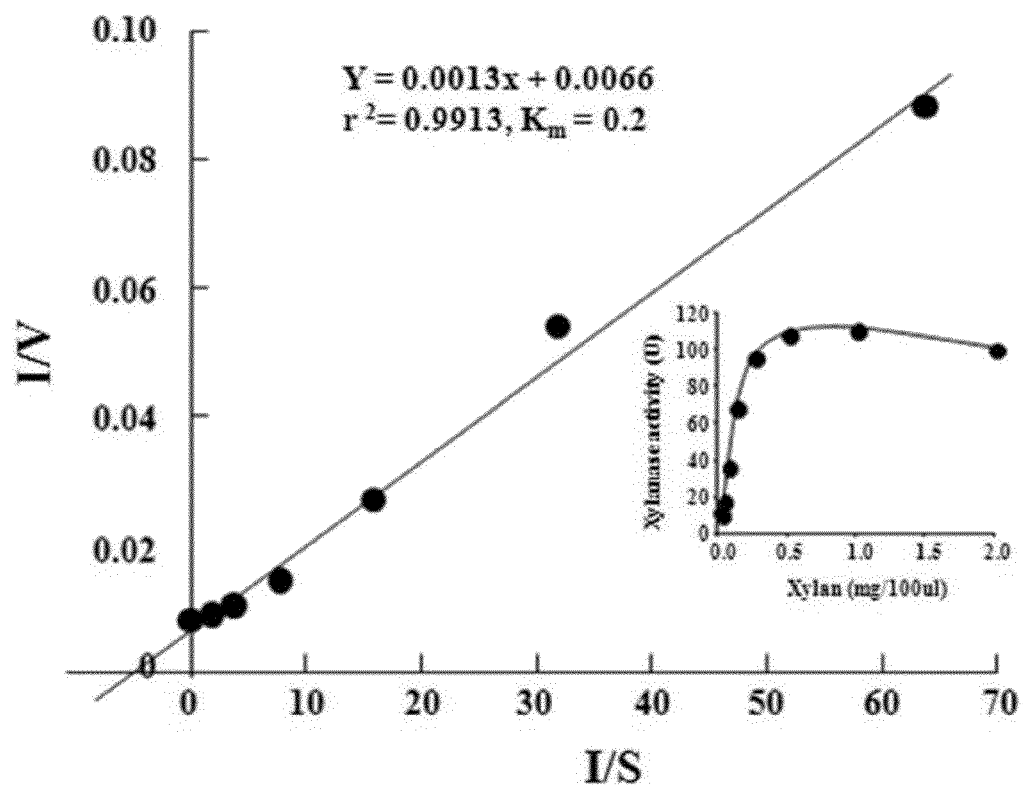
FIG. 7 is a diagram illustrating the kinetics of the separated and purified xylanase.

As a result, as shown in FIG. 7, affinity $K_m$ value to xylan substrate was 0.2. Most of the hydrolyzates were xylose and xylo-oligomer. Xylanase activity against other xylans (beech, oats, etc) was similar to that against birch xylan.

INDUSTRIAL APPLICABILITY

As explained hereinbefore, unlike the conventional xylanase, the novel xylanase of the present invention shows high activity in a wide range of pH and excellent heat-resistance to decompose xylan, the major component of various lignocellulosic biomass, so that it can not only be used for the preparation and development of a xylan decomposer, a composition for food processing, a feed additive, or a composition for papermaking process, but also contribute to biochemical industry via the application to the development of bio-fuel, alternative material, performance chemical, and bio-polymer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A Xylanase having
   a) the amino acid sequence set forth as SEQ. ID. NO: 4;
   b) the amino acid sequence having at least 90% homology with the amino acid sequence set forth as SEQ. ID. NO: 4;
   c) the amino acid sequence encoded by the nucleotide sequence set forth as SEQ. ID. NO: 3; or
   d) the amino acid sequence encoded by DNA hybridized with the DNA containing the nucleotide sequence set forth as SEQ. ID. NO: 3 in the strict condition comprising at least two washings in 0.1×SSC, 0.1% SDS at 65° C., which is identical in its function to the protein containing the amino acid sequence set forth as SEQ. ID. NO: 4;
   wherein the xylanase has the characteristics (i)-(iii);
   (i) molecular weight: approximately 65 KDa on SDS-PAGE;
   (ii) maximum activity in the range pH 5-pH 11; and
   (iii) maximum activity at the temperature of 50-60° C.

2. A transformant to which a recombinant expression vector is introduced, in which polynucleotide encoding the xylanase of claim 1 is operably linked to the recombinant expression vector.

3. The transformant according to claim 2, wherein the polynucleotide has one of the following sequences:
   a) the nucleotide sequence set forth as SEQ. ID. NO: 3;
   b) the nucleotide sequence having 90% homology with the nucleotide sequence represented by SEQ. ID. NO: 3;
   c) the nucleotide sequence encoding the amino acid sequence set forth as SEQ. ID. NO: 4; and
   d) the nucleotide sequence comprising DNA sequence to be hybridized with DNA containing the nucleotide sequence set forth as SEQ. ID. NO: 3 under the strict condition comprising at least two washings in 0.1×SSC, 0.1% SDS at 65° C. and encoding the protein haying the same function as the protein comprising the amino acid sequence set forth as SEQ. ID. NO: 4.

4. The production method of xylanase of claim 1 comprising the steps of:
   a) obtaining crude enzyme solution by centrifugation after culturing Paenibacillus sp. HPL-3 strain in a medium; and
   b) purifying xylanase from the crude enzyme solution of step a).

5. The production method according to claim 4, wherein the strain is Paenibacillus sp. HPL-3 deposited under the Accession No. of KCTC11987BP.

6. The production method according to claim 4, wherein the xylanase has one of the following sequences:
   a) the amino acid sequence set forth as SEQ. ID. NO: 3;
   b) the amino acid sequence having 95% homology with the amino acid sequence represented by SEQ. ID. NO: 3;
   c) the amino acid sequence encoded by the nucleotide sequence represented by SEQ. ID. NO: 4; and
   d) the amino acid sequence encoded by DNA hybridized with the DNA containing the nucleotide sequence set forth as SEQ. ID. NO: 3 in the strict condition comprising at least two washings in 0.1×SSC, 0.1% SDS at 65° C., which is identical in its function to the protein containing the amino acid sequence set forth as SEQ. ID. NO: 4.

* * * * *